(12) United States Patent
Waisblatt et al.

(10) Patent No.: US 9,408,687 B2
(45) Date of Patent: *Aug. 9, 2016

(54) TISSUE MODIFICATION

(71) Applicant: Boston Scientific Scimed, Inc., Maple Grove, MN (US)

(72) Inventors: Jarad Waisblatt, Sunnyvale, CA (US); Benjamin Sutton, Scotts Valley, CA (US); Ali Salahieh, Saratoga, CA (US); Peter W. Gregg, Santa Cruz, CA (US); Crystal M. Anderson-Cunanan, Mission Viejo, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/739,909

(22) Filed: Jun. 15, 2015

(65) Prior Publication Data

US 2015/0272717 A1   Oct. 1, 2015

Related U.S. Application Data

(63) Continuation of application No. 14/481,477, filed on Sep. 9, 2014, now Pat. No. 9,056,007, which is a continuation of application No. 13/626,578, filed on Sep. 25, 2012, now Pat. No. 8,834,349.

(60) Provisional application No. 61/539,675, filed on Sep. 27, 2011.

(51) Int. Cl.
    *A61F 2/04*    (2013.01)
    *A61F 2/02*    (2006.01)
    *A61F 2/24*    (2006.01)

(52) U.S. Cl.
    CPC ............... *A61F 2/02* (2013.01); *A61F 2/2415* (2013.01)

(58) Field of Classification Search
    CPC .......... A61F 2/02; A61F 2/062; A61F 2/2415
    USPC .............. 600/36; 128/897–898; 623/915, 920
    See application file for complete search history.

(56) References Cited

U.S. PATENT DOCUMENTS 1,919,649 A   7/1933   Griffin et al.
2,185,441 A   1/1940   Juueczki (Continued)

FOREIGN PATENT DOCUMENTS

WO       WO 96/06192       2/1996

OTHER PUBLICATIONS

Langdon et al., "Biaxial Mechanical/Structural Effects of Equibiaxial Strain During Crosslinking of Bovine Pericardial Xenograft Materials," *Biomaterials*, 1999, 20:137-153.

(Continued)

*Primary Examiner* — John Lacyk
(74) *Attorney, Agent, or Firm* — Pauly, DeVries Smith & Deffner, L.L.C.

(57) ABSTRACT

A tissue modification apparatus includes a first and a second guide, a first and a second set of mounts, and a first and a second actuator. The first guide defines a first axis, and the second guide defines a second axis intersecting the first axis. The mounts of the first set of mounts are movable relative to one another along the first axis, and the mounts of the second set of mounts are movable relative to one another along the second axis. The first actuator and the second actuator are each settable to a stress load, with the first actuator and the second actuator movable, respectively, along the first axis and the second axis to transmit each respective stress load to a piece of tissue mechanically coupled to the first and second set of mounts.

20 Claims, 11 Drawing Sheets

(56) References Cited

U.S. PATENT DOCUMENTS

| | | |
|---|---|---|
| 2,594,902 A | 4/1952 | Frazier |
| 4,681,588 A | 7/1987 | Ketharanathan |
| 4,800,603 A | 1/1989 | Jaffe |
| 5,298,012 A | 3/1994 | Handlos |
| 5,902,228 A | 5/1999 | Schulsinger et al. |
| 6,796,977 B2 | 9/2004 | Yap et al. |
| 7,622,276 B2 | 11/2009 | Cunanan et al. |
| 8,137,411 B2 | 3/2012 | Schankereli |
| 8,834,349 B2 | 9/2014 | Waisblatt et al. |
| 9,056,007 B2 * | 6/2015 | Waisblatt .............. A61F 2/2415 |
| 2009/0069880 A1 | 3/2009 | Vonderwalde et al. |
| 2013/0012767 A1 | 1/2013 | Nguyen et al. |

OTHER PUBLICATIONS

Zioupos et al., "Anisotropic Elasticity and Strength of Glutaraldehyde Fixed Bovine Pericardium for Use in Pericardial Bioprosthetic Valves," *J Biomedical Materials Res*, 1994, 28:49-57.

International Invitation to Pay Additional Fees in International Application No. PCT/US2015/041334, dated Nov. 11, 2015, 5 pages.

* cited by examiner

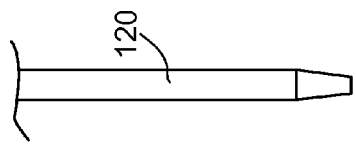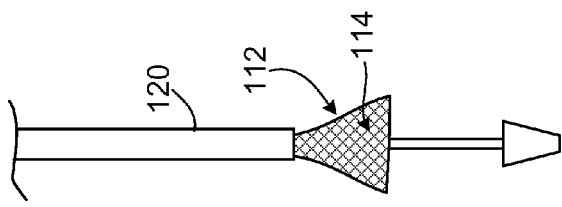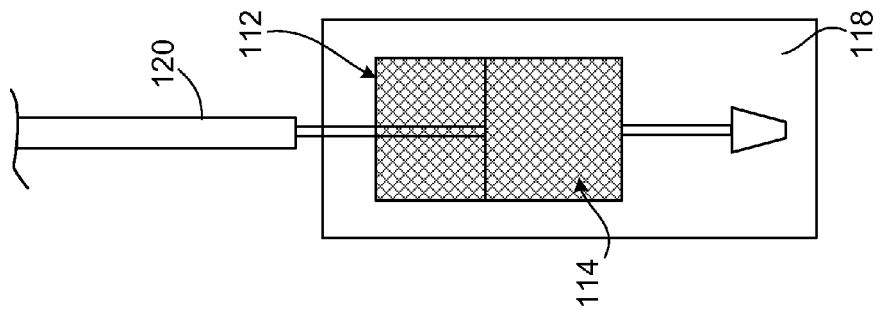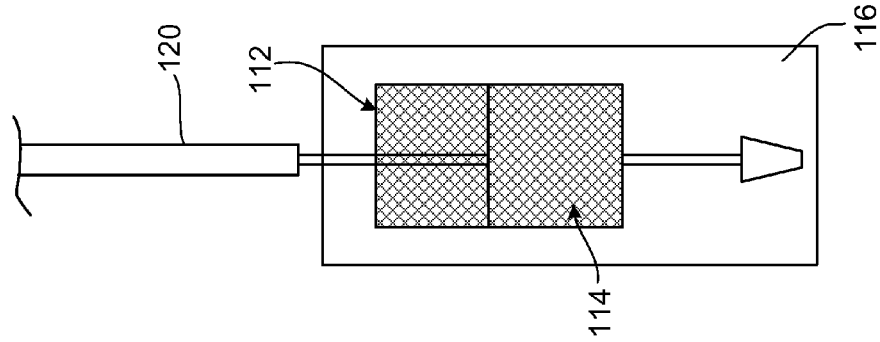
FIG. 11D
FIG. 11C
FIG. 11B
FIG. 11A

TISSUE MODIFICATION

CROSS-REFERENCE TO RELATED APPLICATIONS

This application is a continuation of U.S. application Ser. No. 14/481,477 file Sep. 9, 2014, which is a continuation of U.S. application Ser. No. 13/626,578 filed Sep. 25, 2012, which claims the benefit of U.S. Provisional Application Ser. No. 61/539,675, filed on Sep. 27, 2011, which is incorporated by reference herein.

TECHNICAL FIELD

The following disclosure relates to tissue modification and, more particularly, to modification of biological tissue for implantation in a mammal.

BACKGROUND

Heart valve surgery can be used to repair or replace diseased heart valves. For example, heart valve replacement may be indicated when there is a narrowing of the native heart valve, commonly referred to as stenosis, or when the native valve leaks or regurgitates. The repair or replacement of diseased heart valves can include, for example, the introduction of a prosthetic heart valve that includes biological tissue heterologous to the patient (e.g., a heterograft or xenograft).

Biological tissue can have mechanical properties that vary within a single donor and/or from among several donors of the same species. For example, biological tissue from a single donor can have non-uniform thickness, and the average thickness of biological tissue can vary from one donor to another. The variation in mechanical properties of biological tissue used in replacement heart valves can impact the performance and/or durability of a replacement heart valve implanted in a patient.

SUMMARY

Tissue modification changes one or more mechanical properties of biological tissue used for implantation in a mammal.

In one aspect, a tissue modification apparatus includes a first and a second guide, a first and a second set of mounts, and a first and a second actuator. The first guide defines a first axis, and the second guide defines a second axis intersecting the first axis. The mounts of the first set of mounts are movable relative to one another along the first axis, and the mounts of the second set of mounts are movable relative to one another along the second axis. The first actuator and the second actuator are each settable to a stress load, with the first actuator and the second actuator movable, respectively, along the first axis and the second axis to transmit each respective stress load to a piece of tissue mechanically coupled to the first and second set of mounts.

In some embodiments, the second axis is substantially perpendicular to the first axis. In certain embodiments, the second axis intersects the first axis in a plane substantially parallel to a substantially planar surface of the piece of tissue mechanically coupled to the first and second set of mounts.

In some embodiments, at least a portion of the first guide is mechanically coupled to at least a portion of the second guide. For example, the first guide can be mechanically coupled to the second guide at the intersection of the first axis and the second axis.

In certain embodiments, a plurality of first guides is substantially parallel to or coaxial with the first axis and a plurality of second guides is substantially parallel to or coaxial with the second axis. For example, the plurality of first guides can include a first pair of rods substantially parallel to one another and the plurality of second guide can include a second pair of rods substantially parallel to one another. Additionally or alternatively, at least one of the first pair of rods is disposed along the first axis and at least one of the second pair of rods is disposed along the second axis. Each rod of the first and second pair of rods can have an outer diameter great than or equal to about 0.75 mm and less than or equal to about 13 mm. For example, each rod of the first and second pair of rods is stainless steel with an outer diameter of about 3.2 mm.

In some embodiments, the first pair of rods are substantially perpendicular to the second pair of rods to form a substantially cruciform frame with an aperture defined by the first pair of rods and the second pair of rods and portions of each of the first and second pair of rods extending away from the aperture. For example, the first actuator and the second actuator are disposed on the respective portions of the first and second pair of rods extending away from the aperture. Additionally or alternatively, the first set of mounts and the second set of mounts are disposed on the respective portions of the first and second pair of rods extending away from the aperture.

In certain embodiments, the first guide and the second guide each include at least one passivated surface. Additionally or alternatively, the first guide and the second guide can each include at least one polished surface.

In some embodiments, the first guide and the second guide each include at least one collar stationary relative to the respective first and second guide. The at least one collar can be disposed along the respective first and second axes, and the at least one collar can limit movement of the respective first and second set of mounts along the respective first and second axes.

In certain embodiments, each mount of the first set of mounts is larger than each of the second set of mounts along axes perpendicular to the respective first and second axes. For example, each mount of the first set of mounts can extend about 100 mm to about 150 mm in a direction perpendicular to the first axis and each mount of the second set of mounts can extend about 50 mm to about 90 mm in a direction perpendicular to the second axis. In some embodiments, each mount of the first set of mounts and the second set of mounts is substantially cylindrical with an outer diameter of about 6 mm to about 25 mm.

In some embodiments, each mount of the first and second set of mounts includes mitered end portions. For example, the mitered end portions of each mount of the first set of mounts can be complementary to the mitered end portions of each mount of the second set of mounts.

In certain embodiments, the first and second actuators are each movable along the respective first and second axes to transmit each respective set stress load substantially simultaneously to a piece of tissue.

In some embodiments, the first and second actuators each comprise at least one spring. For example, the at least one spring of each first and second actuator can be compressible to set the respective stress load and expandable transmit the respective stress load to the piece of tissue mechanically coupled to the first and second set of mounts. The at least one spring of the first actuator and the at least one spring of the second actuator can have substantially similar spring constants. Additionally or alternatively, the at least one spring of the first actuator and the at least one spring of the second actuator can have spring constants of about 5 N/m to about 50 N/m. Additionally or alternatively, the at least one spring of the first actuator and the at least one spring of the second actuator can each be compressible from respective equilibrium positions by a distance of about 5 mm to about 35 mm.

In certain embodiments, each mount of the first and second set of mounts includes at least one surface in slidable contact with the respective first and second guides along the respective first and second axes. For example, the at least one surface of each of the first and second sets of mounts in slidable contact with the respective first and second guides is polytetrafluoroethylene.

In some embodiments, each mount of the first and second set of mounts comprises a bearing in rolling contact with a respective first and second guide. For example, each bearing can be polyoxymethylene or polytetrafluoroethylene. Additionally or alternatively, each bearing can be a flange bearing.

In certain embodiments, each mount of the first and second set of mounts comprises a plurality of hooks extending away from each respective mount. For example, each of the plurality of hooks can be substantially axially aligned with one another along each respective mount. Additionally or alternatively, the plurality of hooks can be substantially evenly spaced along the axis.

In another aspect, a tissue modification system includes a tissue stretcher and a jig. The tissue stretcher includes a first guide and a second guide, a first set of mounts and a second set of mounts, a first actuator and a second actuator. The first guide defines a first axis, and the second guide defines a second axis intersecting the first axis. The mounts of first set of mounts are movable relative to one another along the first axis, and the mounts of the second set of mounts are movable relative to one another along the second axis. The first actuator and the second actuator are mechanically coupled, respectively, to the first and second set of mounts. The jig includes a base, a support extending from the base, and a plurality of locking members. The first guide and/or the second guide are mechanically couplable to the base such that the first and second guides are stationary relative to the base. The plurality of locking members are mechanically couplable to the base and movable with respect to the first and second actuators to allow movement of the first and second actuators along the respective first and second axes to transmit a respective stress load to a piece of tissue mechanically coupled to the first and second set of mounts.

In some embodiments, the first and second actuators are movable relative to the base to set respective stress loads and the plurality of locking members are movable to hold the first and second actuators at the respective set stress loads.

In certain embodiments, the support and the locking members are simultaneously mechanically decouplable from the tissue stretcher.

In some embodiments, the first guide includes a first pair of rods substantially parallel to one another and the second guide includes a second pair of rods substantially parallel to one another. For example, the first pair of rods can be substantially perpendicular to the second pair of rods to form a substantially cruciform frame with an aperture defined by the first pair of rods and the second pair of rods and portions of each of the first and second pair of rods extending away from the aperture. At least a portion of the support can be engageable with the aperture to hold the first and second pair of rods stationary relative to the base. Additionally or alternatively, the first actuator and the second actuator can be disposed on the respective portions of the first and second pair of rods extending away from the aperture. Additionally or alternatively, the first set of mounts and the second set of mounts can be disposed on the respective portions of the first and second pair of rods extending away from the aperture.

In another aspect, a tissue modification method includes moving a first pair of mounts toward one another along a first axis to set a first load, moving a second pair of mounts toward one another along a second axis, intersecting the first axis, to set a second load, mechanically coupling a substantially planar sheet of tissue to the first pair of mounts and to the second pair of mounts, moving the first pair of mounts away from one another along the first axis to apply the set first load to the substantially planar sheet of tissue, and moving the second pair of mounts away from one another along the second axis to apply the set second load to the substantially planar sheet of tissue.

In some embodiments, the first axis is substantially perpendicular to the second axis. In certain embodiments, the first stress load is substantially equal to the second stress load. In some embodiments, the first stress load and the second stress load are applied parallel to the substantially planar surface of the tissue. In certain embodiments, the first and second set stress loads are applied substantially simultaneously.

In certain embodiments, moving the first and second pair of mounts toward one another along the respective first and second axes includes compressing one or more springs mechanically coupled to the first and second pair of mounts. Additionally or alternatively, moving the first and second pair of mounts away from one another along the respective first and second axes can include at least partially releasing the compression of the one or more springs mechanically coupled to the first and second pair of mounts.

In another aspect, a tissue modification method includes setting a first and a second stress load to apply to a piece of tissue, applying the first stress load to the piece of tissue along a first axis, and applying the second stress load to the piece of tissue along a second axis substantially perpendicular to the first axis, wherein the first and second stress loads are applied to the tissue substantially simultaneously.

In certain embodiments, setting the first and second stress loads includes compressing respective first and second springs. Additionally or alternatively, applying the first and second stress loads includes at least partially releasing the respective compressed first and second springs.

In some embodiments, the first stress load and the second stress load are substantially equal.

In certain embodiments, the piece of tissue is a substantially planar sheet and the first and second axes are parallel to the plane defined by the substantially planar sheet. Additionally or alternatively, the piece of tissue includes biological tissue. For example, the piece of tissue can be one of bovine pericardium, equine pericardium, and porcine pericardium.

In some embodiments, the piece of tissue is exposed to a glutaraldehyde solution. Additionally or alternatively, the piece of tissue can be exposed to the glutaraldehyde solution during at least a portion of the exposure of the piece of tissue to the first and second stress loads. For example, the piece of tissue can be exposed to glutaraldehyde solution for about one day to about two weeks. The first and second stress loads can be each applied to the piece of tissue for about 30 minutes to about 120 minutes.

In another aspect, a tissue modification method includes arranging a substantially planar patch of pericardial tissue in a stationary position relative to a base, and moving a shaver relative to the substantially planar patch of pericardial tissue to remove tissue along at least a portion of a substantially planar surface of the substantially planar patch of pericardial tissue.

In some embodiments, the substantially planar patch of pericardial tissue has a first substantially planar surface rougher than a second substantially planar surface. The shaver can remove at least a portion of the first substantially planar surface.

In certain embodiments, the substantially planar patch of pericardial tissue is bovine pericardium, equine pericardium, or porcine pericardium.

In some embodiments, vacuum pressure is applied to the substantially planar patch of pericardial tissue such that the substantially planar patch of pericardial tissue is drawn toward the base. For example, the vacuum pressure is applied to the substantially planar patch of tissue by drawing air through a plurality of orifices defined by the base. Additionally or alternatively, a saline solution can be applied to the substantially planar piece of tissue. For example, the saline solution and the vacuum pressure can be simultaneously applied to the substantially planar piece of tissue.

In certain embodiments, the substantially planar piece of tissue is fixed and the shaver is moved relative to the stationary piece of tissue during or after fixing the substantially planar piece of tissue.

In another aspect, a tissue modification method includes forming a substantially planar leaflet from a piece of pericardial tissue, arranging the substantially planar leaflet in a stationary position relative to a base, and removing tissue from at least a portion of a substantially planar surface of the substantially planar leaflet. The substantially planar leaflet includes a coaptation portion, an arcuate edge substantially opposite the coaptation portion, the arcuate edge having a first end and a second end, and a belly extending from the arcuate edge to an axis defined by the first and second ends of the arcuate edge.

In certain embodiments, removing at least a portion of the substantially planar surface of the substantially planar leaflet includes removing tissue from the belly of the leaflet. Additionally or alternatively, removing at least a portion of the substantially planar surface of the substantially planar leaflet includes moving a laser (e.g., a femtosecond laser) over a portion of the stationary, substantially planar leaflet.

In another aspect, a method of prosthetic heart valve preparation includes storing a prosthetic heart valve in a first solution, the prosthetic heart valve comprising a biological tissue isotonic to the first solution, exposing the biological tissue of the prosthetic heart valve to a second solution hypertonic to the biological tissue such that water flows out of the biological tissue, and moving a sheath distally over the prosthetic heart valve to contract the prosthetic heart valve for intraluminal delivery to a mammalian heart.

In some embodiments, the second solution is about 75 percent to about 80 percent water. In certain embodiments, the tonicity of the second solution is about 339 mOsm/L to about 12.3 Osm/L. Additionally or alternatively, the biological tissue of the prosthetic heart valve can be exposed to the second solution for about 30 seconds to about 15 minutes. Additionally or alternatively, the first solution and the second solution can be at substantially the same temperature.

In certain embodiments, the biological tissue is sterilized (e.g., in a terminal sterilization procedure) after the biological tissue of the prosthetic heart valve is exposed to the second solution hypertonic to the biological tissue. For example, sterilizing the biological tissue can include exposing the biological tissue to electron beam (e-beam) radiation and/or exposing the biological tissue to ethylene oxide (EtO).

In another aspect, a method of prosthetic heart valve preparation includes exposing a prosthetic heart valve in a first solution, the prosthetic heart valve comprising a biological tissue isotonic to the first solution, exposing the biological tissue of the prosthetic heart valve to a second solution including alcohol or ethylene glycol such that water flows out of the biological tissue, and moving a sheath distally over the prosthetic heart valve to contract the prosthetic heart valve for intraluminal delivery to a mammalian heart. In some embodiments, exposing the biological tissue of the prosthetic heart valve to the second solution includes exposing the biological tissue to a series of graded alcohol solutions or a series of graded ethylene glycol solutions. For example, the series of graded alcohol or ethylene glycol solutions includes about 50%, about 60%, about 70%, about 90%, about 95%, and about 100% alcohol or ethylene glycol solutions.

In some embodiments, the biological tissue of the prosthetic heart valve is exposed to the second solution for about 30 seconds to about 15 minutes. Additionally or alternatively, the first solution and the second solution can be at substantially the same temperature.

In certain embodiments, the biological tissue is sterilized (e.g., in a terminal sterilization procedure) after the biological tissue of the prosthetic heart valve is exposed to the second solution including alcohol or ethylene glycol. For example, sterilizing the biological tissue can include exposing the biological tissue to electron beam (e-beam) radiation and/or exposing the biological tissue to ethylene oxide (EtO).

In still another aspect, a method of prosthetic heart valve preparation includes exposing a biological tissue to a first solution, exposing the biological tissue to a second solution such that water flows out of the biological tissue, and applying biaxial stress loads to the biological tissue. The biological tissue is isotonic to the first solution. The second solution includes alcohol or ethylene glycol. The biaxial stress load can be applied to the biological tissue after the biological tissue is exposed to the second solution.

Embodiments can include one or more of the following advantages.

In some embodiments, stress loads to be transmitted to tissue can be set prior to being applied to a respective first axis and a second axis. Setting the stress loads in this manner can allow biaxial stress to be repeatably and reliably applied to multiple, different pieces of tissue. This repeatable and reliable application of stress load can improve the amount of tissue that can be processed, as compared to methods that require more manual manipulation by an operator.

Moreover, setting the stress load in these embodiments results in a set stress to the tissue and variable amount of strain applied to pieces of tissue. For example, in these embodiments, pieces of tissue having different stress-strain characteristics will be stretched different distances under the same set stress load. Setting the stress load and allowing the resulting strain in the tissue to vary can improve the uniformity of the mechanical properties (e.g., stiffness along a first axis and a second axis) across several pieces of tissue. This improved uniformity can facilitate tissue matching for leaflets used in a prosthetic heart valve, where matching mechanical properties of the tissue used for the leaflets can improve the load distribution over the leaflets and, thus, improve hemodynamic performance and/or improve the durability of the prosthetic heart valve.

In certain embodiments, set stress loads are applied substantially simultaneously along the respective first and second axes. As compared to biaxial stress load that is not applied substantially simultaneously, the application of substantially simultaneous biaxial stress load to tissue to apply a substantially simultaneous stress to the tissue can improve the mechanical properties of the tissue. For example, exposing tissue to substantially simultaneous biaxial stress loading can improve the similarity between stiffness of the tissue along the first and second axes. In a prosthetic heart valve including leaflets made from tissue, the improvements in the similarity in stiffness characteristics along the first and second axes of the tissue can result in improved load distribution and/or durability in the valve.

In some embodiments, a shaver is moved relative to a planar patch of pericardial tissue to remove tissue along at least a portion of the substantially planar surface of the substantially planar patch of pericardial tissue. This removal of tissue can improve the uniformity of thickness of the planar patch of tissue. In instances in which the tissue or a portion of the tissue is part of an intraluminally delivered prosthetic heart valve, the improved uniformity of thickness of the tissue can result in reduced forces associated with sheathing the prosthetic heart valve for intraluminal delivery.

In certain embodiments, the substantially planar patch of pericardial tissue has a first substantially planar surface rougher than a second substantially planar surface and the shaver is moved relative to the planar patch of pericardial tissue to remove tissue from the rougher surface. Removal of tissue from the rougher substantially planar surface of the pericardial tissue can decrease the thickness profile of the tissue while substantially maintaining the overall mechanical properties of the tissue.

In certain embodiments, a laser is moved relative to a substantially planar leaflet to remove tissue from at least a portion of a substantially planar surface of the substantially planar leaflet. By selectively removing material from portions of the substantially planar leaflet (e.g., the belly of the leaflet), the laser can be used to achieve a local reduction in thickness of the tissue. This local reduction in the thickness of the tissue can reduce the forces associated with sheathing a prosthetic heart valve for intraluminal delivery while maintaining the thickness of the leaflet in other areas to facilitate attachment and/or to improve load distribution.

In certain embodiments, biological tissue of a prosthetic heart valve is exposed to a solution hypertonic to the biological tissue such that water flows out of the biological tissue. In some embodiments, biological tissue of a prosthetic heart valve is exposed to a solution including alcohol or ethylene glycol such that water flows out of the biological tissue. Such removal of water from the biological tissue reduces one or more dimensions of the biological tissue such that forces associated with sheathing the prosthetic heart valve are reduced. Additionally or alternatively, such reduction of one or more dimensions of the biological tissue can facilitate reduction of the overall outer diameter of the inraluminal delivery system for the prosthetic heart valve.

In certain embodiments, the tissue can be dehydrated (e.g., by exposure to a hypertonic solution, alcohol, or ethylene glycol) during the final manufacturing steps of a prosthetic heart valve such that the tissue undergoes terminal sterilization in a dehydrated state. As compared to tissue in a hydrated state, the tissue in a dehydrated state can better withstand exposure to forms of terminal sterilization (e.g., e-beam and ethylene oxide sterilization) that tend to damage and/or alter biological tissue in a hydrated state. Additionally or alternatively, the dehydration of the biological tissue can facilitate sterilization and storage of the prosthetic heart valve in a sheathed or unsheathed position. This can, for example, facilitate the sterilization of the entire prosthetic heart valve assembly (including the valve, valve delivery system, and handle, etc.) in a single package, without the need, for example, for storing the valve in liquid.

The details of one or more embodiments of the invention are set forth in the accompanying drawings and the description below. Other aspects, features, and advantages of the invention will be apparent from the description and drawings, and from the claims.

DESCRIPTION OF DRAWINGS

FIGS. 11A-D are schematic representations of the process of sheathing a prosthetic heart valve including biological tissue.

Like reference symbols in the various drawings indicate like elements.

DETAILED DESCRIPTION

Referring to FIGS. 1-6, a tissue modification system 1 includes a tissue stretcher 10 and a jig 50. In use, as described in further detail below, the tissue stretcher 10 is mechanically couplable to the jig 50 such that at least a portion of the tissue stretcher 10 remains fixed in place relative to the jig 50 and a substantially planar piece of tissue 70 can be mounted on the tissue stretcher 10. As also described in further detail below, the tissue stretcher 10 can be decoupled from the jig 50 such that at least a portion of the tissue stretcher 10 expands to stretch the tissue 70 biaxially.

Figure 1:
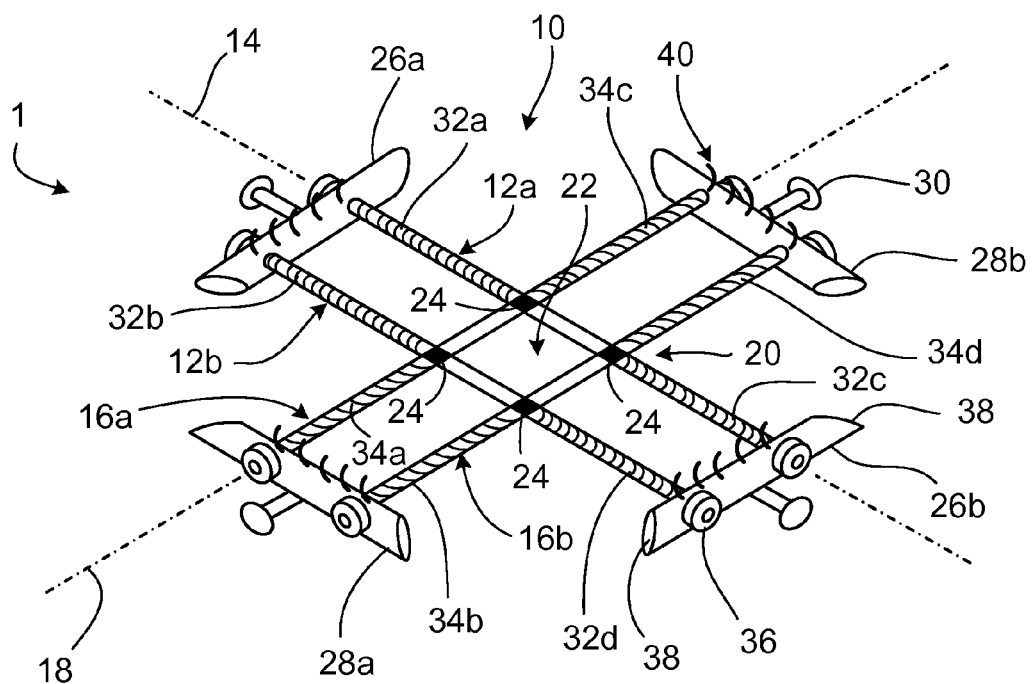
FIG. 1 is a partially exploded isometric view of a tissue modification system.
Figure 1:
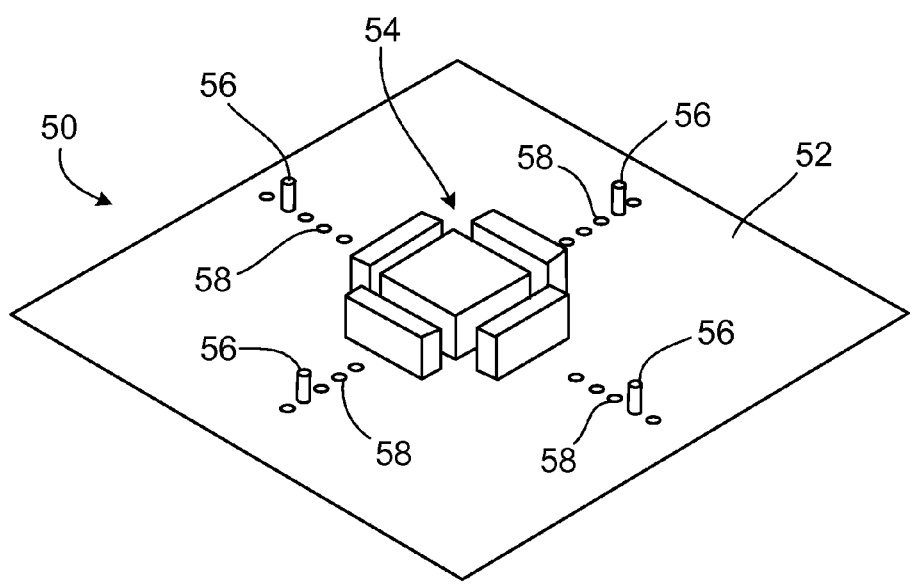
Figure 2:
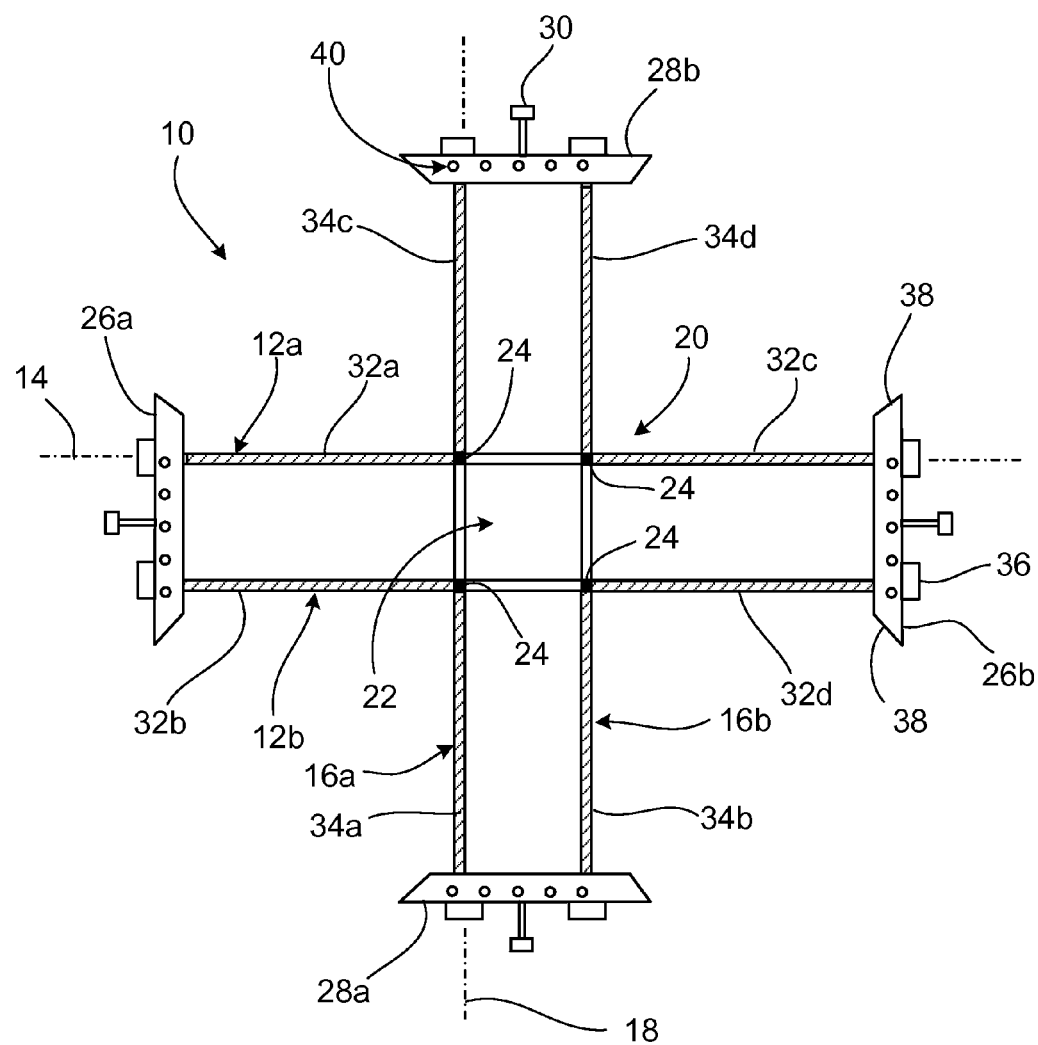
FIG. 2 is a top view of a tissue stretcher of the tissue modification system of FIG. 1.

Referring now to FIGS. 1-2, the tissue stretcher 10 includes first mounts 26a,b disposed along substantially parallel first guides 12a,b and second mounts 28a,b disposed along substantially parallel second guides 16a,b. First actuators 32a,b,c,d are disposed on the first guides 12a,b and second actuators 34a,b,c,d are disposed on the second guides 16a,b. In use, the first actuators 32a,b,c,d can move the first mounts 26a,b away from one another along a first axis 14 defined by one of the first guides 12a,b, and the second actuators 34a,b,c,d can move the second mounts 28a,b away from one another along a second axis 18 defined by one of the second guides 16a,b. The relative movement of the first mounts 26a,b away from one another along the first axis 14 and the relative movement of the second mounts 28a,b away from one another along the second axis 18 results in the application of a biaxial stress load to tissue (e.g., the tissue 70 in FIGS. 5-6) mounted on the tissue stretcher 10.

As used herein, "stress load" is the force (measured, e.g., in N) applied to the tissue. For example, in some embodiments in which the first actuators 32a,b,c,d and the second actuators 34a,b,c,d are springs, the stress load is proportional to the spring constant and the displacement of the spring from its equilibrium position. In these embodiments, the stress load can be mathematically expressed by Hooke's law ($F=-k \cdot x$, where F is the stress load, k is the spring constant, and x is the displacement of the spring's end from it equilibrium position). As used herein, "stress" is the force (i.e., stress load) per unit area of the tissue and can be measured, for example, in N/mm². Accordingly, the stress applied to the tissue is a function of the stress load and the cross-sectional area of the tissue. For example, for a given stress load, the stress applied to the tissue may vary with the thickness of the tissue.

The first guides 12a,b and the second guides 16a,b are coupled (e.g., welded, interference fit) to one another at connection regions 24 defined by the intersection of the first guides 12a,b with the second guides 16a,b (e.g., the intersection of the first axis 14 and the second axis 18). The mechanical coupling between the first guides 12a,b and the second guides 16a,b can facilitate the application of biaxial stress load to a piece of the tissue 70 (FIGS. 5-6) mounted on the tissue stretcher 10. In some embodiments, the connection regions 24 are the point of origin of the respective actuation forces transmitted by the respective force actuators 32a,b,c,d and 34a,b,c,d to the respective first mounts 26a,b and second mounts 28a,b.

In some embodiments, the first and second guides 12a,b, 16a,b include at least one polished surface and/or at least one passivated surface. The polished surface can, for example, reduce friction associated with the movement of the respective first and second mounts 26a,b, 28a,b along the respective first and second guides 12a,b, 16a,b. The passivated surface can, for example, improve resistance of corrosion of the first and second guides 12a,b, 16a,b that could otherwise occur through exposure of the first and second guides 12a,b, 16a,b to saline and/or glutaraldehyde solutions.

The first guides 12a,b are substantially perpendicular to the second guides 16a,b in a plane substantially parallel to a substantially planar surface of the tissue 70 (FIGS. 5-6) mechanically coupled to the first and second set of mounts 26a,b, 28a,b. This substantially perpendicular orientation of the first guides 12a,b to the second guides 16a,b forms a cruciform frame 20 with an aperture 22 defined by at least a portion of the first and second guides 12a,b and 16a,b. At least a portion of each of the first guides 12a,b and the second guides 16a,b extend away from the aperture. As described in further detail below, the first actuators 32a,b,c,d and the first set of mounts 26a,b are disposed on the portions of the first guides 12a,b extending away from the aperture 22. Analogously, the second actuators 34a,b,c,d and the second set of mounts 28a,b are disposed on the portions of the second guides 16a,b extending away from the aperture 22. As also described in further detail below, the aperture 22 is releasably engageable with at least a portion of the jig 50 such that the cruciform frame 20 remains fixed relative to the jig 50 to facilitate movement of the first and second set of mounts 26a,b, 28a,b as the respective stress loads are set.

Each of the first guides 12a,b and the second guides 16a,b can be a rod having an outer diameter greater than or equal to about 0.75 mm and less than or equal to about 13 mm. For example, each of the first guides 12a,b and the second guides 16a,b can be a stainless steel rod with an outer diameter of about 3.2 mm. The use of such a rod for the first guides 12a,b and the second guides 16a,b can facilitate sizing of the tissue stretcher 10 for manual manipulation by an operator while providing sufficient rigidity for the application of loads to the tissue to be modified.

A collar 36 can be disposed on one or more of the first guides 12a,b and the second guides 16a,b. The collar 36 can be coupled (e.g., welded, interference fit) in a stationary position relative to one or more of the first guides 12a,b and the second guides 16a,b to limit the range of motion of the respective first and second set of mounts 26a,b, 28a,b. For example, the collar 36 can be coupled to an end portion of the respective first and second guides 12a,b, 16a,b.

Each of the first and second mounts 26a,b, 28a,b is substantially cylindrical (e.g., a right circular cylinder) with a substantially uniform cross-sectional area along the length of the cylinder. For example, each mount 26a,b, 28a,b can have an outer diameter of about 6 mm to about 25 mm (e.g., about 13 mm). Additionally or alternatively, each mount 26a,b, 28a,b can have a length of about 50 mm to about 150 mm (e.g., about 75 mm, about 125 mm). The length of each of the first mounts 26a,b is perpendicular to the first guides 12a,b, and the length of each of the second mounts 28a,b is perpendicular to the second guides 16a,b.

Each mount 26a,b, 28a,b includes a plurality of hooks 40 extending away from an outer surface of each respective mount 26a,b, 28a,b. For example, each hook 40 can extend about 1.5 mm from the surface of each respective mount 26a,b, 28a,b. This hook size can facilitate, for example, secure attachment to the tissue 70 (FIGS. 5-6) while providing a low profile to reduce the likelihood of unintended snagging during handling. The hooks 40 can be substantially axially aligned with one another along the length of the respective first and second mounts 26a,b, 28a,b. Additionally or alternatively, the plurality of hooks 40 can be substantially evenly spaced along the length of each respective mount 26a,b, 28a,b. This axial alignment and substantially uniform spacing of the hooks 40 can result, for example, in substantially uniform application of stress loads to the tissue 70. In some embodiments, each hook 40 formed from a cut mandrel.

Each of the first and second mounts 26a,b, 28a,b has mitered end portions 38 such that the respective mitered end portions 38 of each of the first mounts 26a,b is complementary to the mitered end portions 38 of each of the second mounts 28a,b. These mitered end portions 38 can facilitate setting the biaxial loads to be applied by the tissue stretcher 10 by, for example, allowing the first mounts 26a,b and the second mounts 28a,b to be moved into close proximity with one another (e.g., by abutting the complementary mounts) during loading.

Additionally or alternatively, the length of each of the first mounts 26a,b can be greater than the length of each of second mounts 28a,b. For example, each of the first mounts 26a,b can have a length of about 100 mm to about 150 mm (e.g., about 125 mm), and the second mounts 28a,b can have a length of about 50 mm to about 90 mm (e.g., about 75 mm). This relative difference in the lengths of the first and second mounts 26a,b, 28a,b can also facilitate setting the biaxial loads to be applied by the tissue stretcher 10 by, for example, allowing the first mounts 26a,b and the second mounts 28a,b to be moved into close proximity with one another during loading.

Each mount 26a,b, 28a,b includes at least one surface in slidable contact with the respective first and second guides 12a,b, 16a,b such that the first mounts 26a,b are slidable relative to one another along the first axis 14 and the second mounts 28a,b are slidable relative to one another along the second axis 18. In some embodiments, the at least one surface of the respective mounts 26a,b, 28a,b in slidable contact with the respective first and second guides 12a,b, 16a,b is polytetrafluoroethylene (PTFE), which can result in low friction between the first and second mounts 26a,b, 28a,b and the respective first and second guides 12a,b, 16a,b. Such low friction can be useful for the efficient and consistently uniform transmission of stress loads from the first and second actuators 32a,b,c,d, 34a,b,c,d to the respective mounts 26a,b, 28a,b and, thus, ultimately to the tissue 70 (FIGS. 5-6) to be modified.

Figure 5:
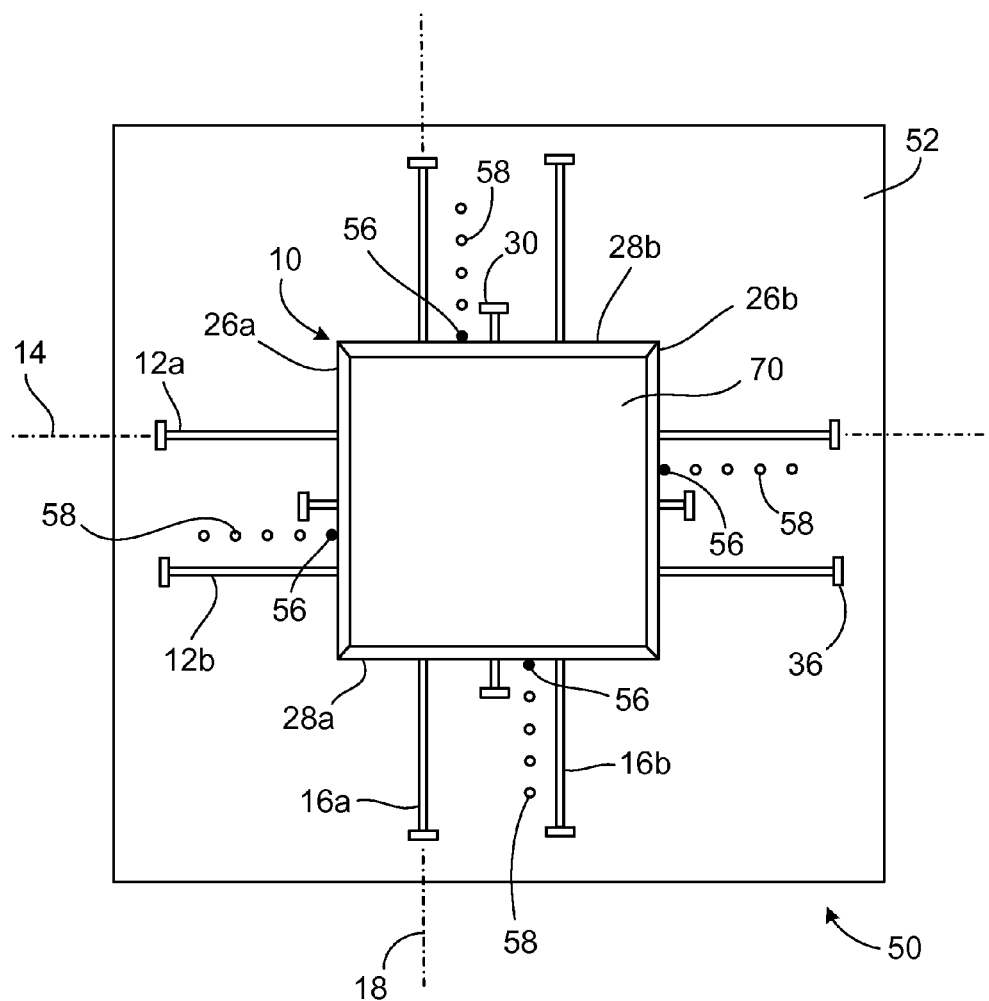
FIG. 5 is a top view of the tissue modification system of FIG. 1 in a compressed state and mounted with tissue.
Figure 6:
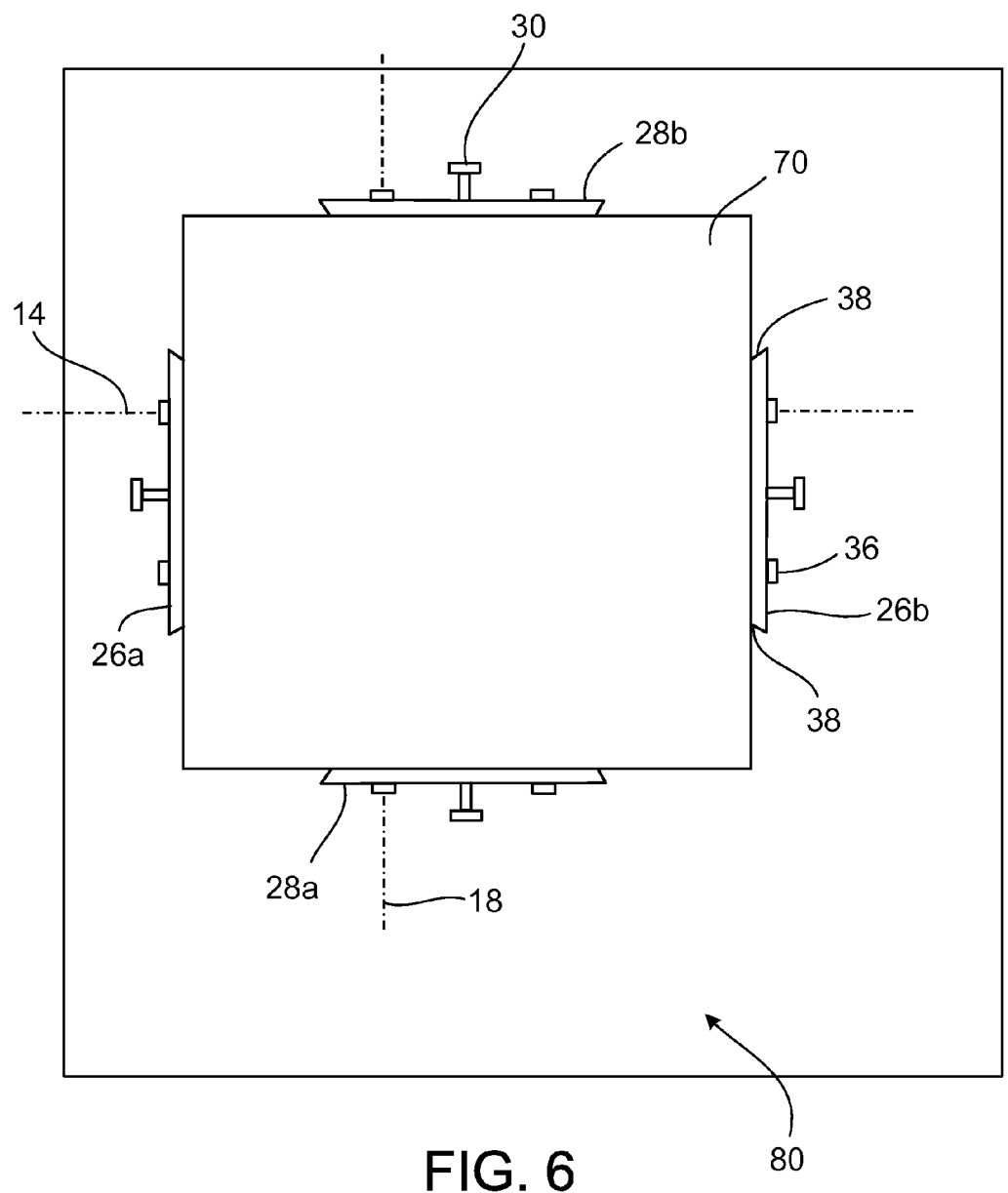
FIG. 6 is a top view of the tissue stretcher of FIG. 1 in an expanded state and mounted with tissue.

The first and second actuators 32a,b,c,d, 34 a,b,c,d are each movable respectively along first and second guides 12a,b, 16a,b. For example, each of the first and second actuators 32a,b,c,d, 34 a,b,c,d can be moved toward the aperture 22 to a fixed position relative to the aperture 22, with this fixed position corresponding to a set (e.g., predetermined) stress load to be applied to the tissue 70 (FIGS. 5-6). As described in further detail below, the first and second actuators 32a,b,c,d, 34 a,b,c,d can be released from this fixed position such that the respective set stress loads are applied to the tissue 70 mounted to the first and second mounts 26a,b, 28a,b. In some embodiments, the relative position of the first and second actuators 32a,b,c,d, 34a,b,c,d with respect to the aperture 22 is proportional to the respective set stress load that will be applied by each actuator to the tissue 70 coupled to the first and second mounts 26a,b, 28a,b.

In some embodiments, the first and second actuators 32a,b,c,d, 34a,b,c,d are substantially simultaneously movable along the respective first and second guides 12a,b, 16,a,b to transmit biaxial stress loads to the tissue 70 (FIGS. 5-6). For example, each of the first and second actuators 32a,b,c,d, 34a,b,c,d can be a spring such that the stress load is set through compression of each spring relative to the equilibrium point of the spring. Each compressed spring can be allowed to expand toward the equilibrium position to move the respective first mounts 26a,b away from one another and/or move the respective second mounts 28a,b away from one another and, thus, apply respective stress loads to the tissue (FIGS. 5-6). Each spring of the first and second actuators 32a,b,c,d, 34a,b,c,d can have a spring constant of about 5 N/m to about 50 N/m. Additionally or alternatively, springs of the first and second actuators 32a,b,c,d, 34a,b,c,d are each compressible from respective equilibrium positions by a distance of about 5 mm to about 35 mm.

In some embodiments, the first and second actuators 32a,b,c,d, 34a,b,c,d are springs having substantially similar spring constants such that the stress loads applied along the first axis 14 and the second axis 18 are substantially equal. In certain embodiments, the first actuators 32a,b,c,d have a spring constant greater than the spring constant of the second actuators 34a,b,c,d such that a larger stress loading can be applied along the first axis 14 than along the second axis 18.

Figure 3:
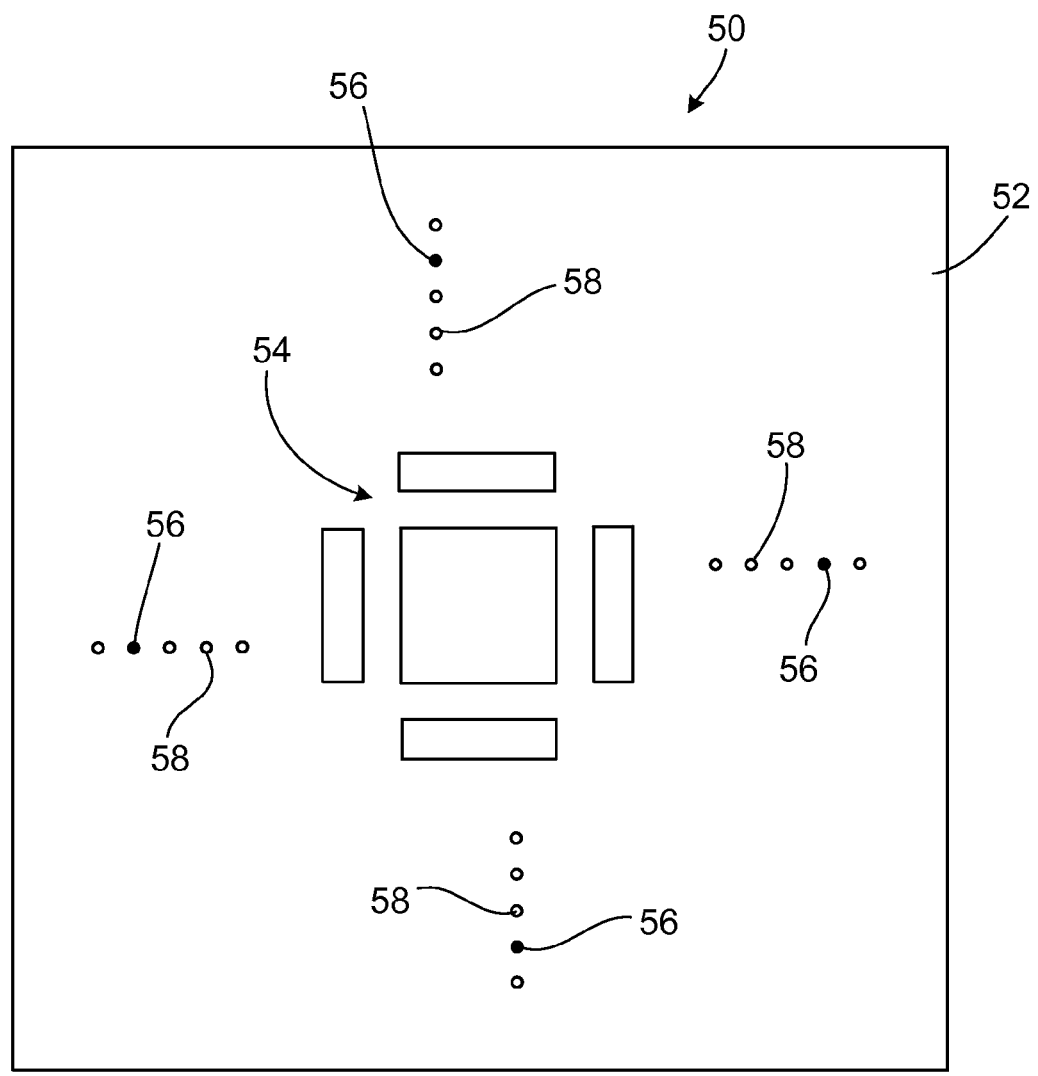
FIG. 3 is a top view of a jig of the tissue modification system of FIG. 1.
Figure 4:
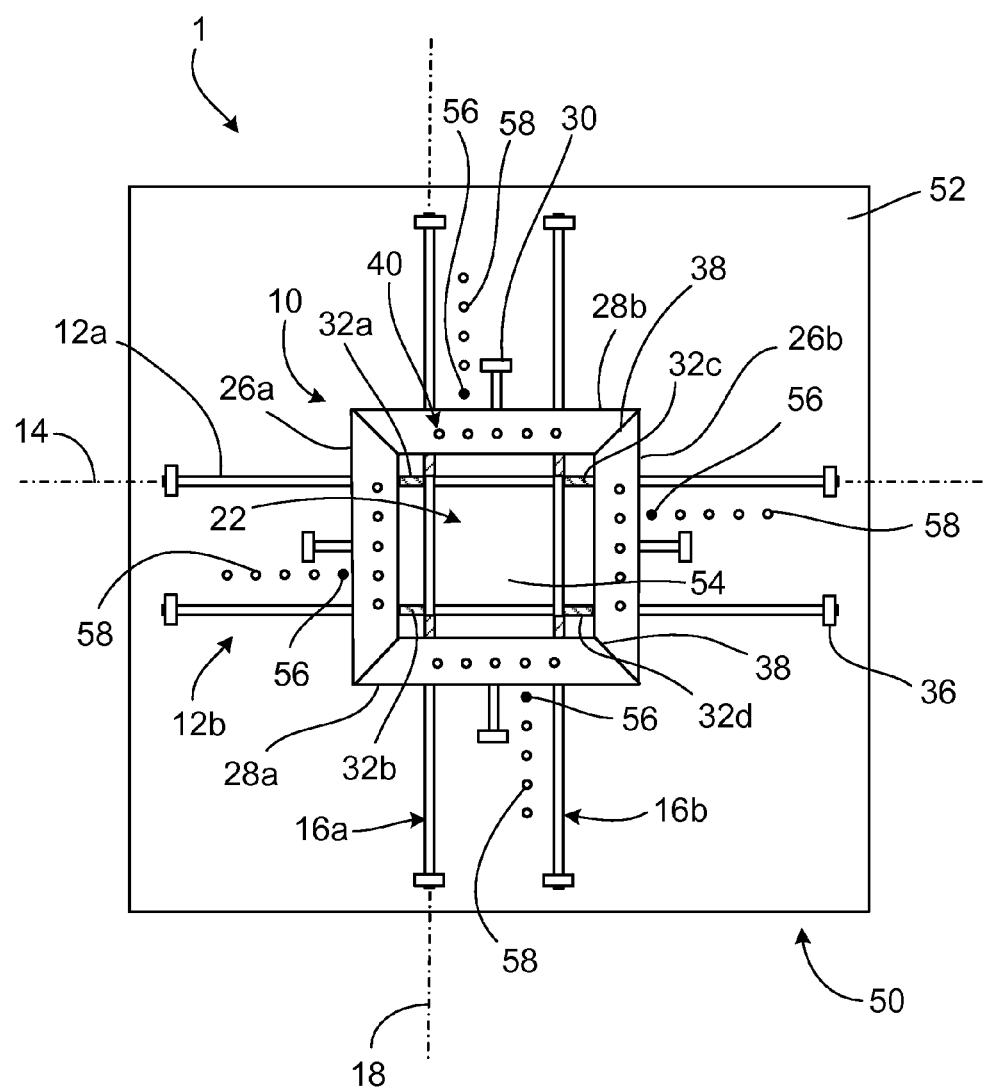
FIG. 4 is a top view of the tissue modification system of FIG. 1 in a compressed state.

Referring now to FIGS. 1, 3, and 4, the jig 50 includes a support 54 extending from a substantially planar base 52. The base 52 defines a plurality of locking apertures 58. Locking members 56 (e.g., pins) are mechanically couplable to the base 52 (e.g., by interference fit with one or more of the locking apertures 58) and extend away from the base 52 on the same side of the base 52 as the support 54. It should be appreciated that the locking members 56 can be disposed in any of the locking apertures 58, as required to set a desired stress load by restricting axial movement of the first and second actuators 32a,b,c,d, 34a,b,c,d. It should be further appreciated that moving the locking members 56 away from the tissue stretcher 10 (e.g., removing the mechanical coupling between the locking members 56 and the first and second actuators 32a,b,c,d, 34a,b,c,d) can allow the respective stress loads to be applied to tissue to be biaxially stretched.

The planar surface of the base 52 can be about as wide and as long as the overall length of the first and second guides 12a,b, 16a,b such that the first and second guides 12a,b, 16a,b can remain supported on the base 52 to provide stability while an operator mounts tissue on the first mounts 26a,b and the second mounts 28a,b. In some embodiments, the base 52 is a substantially rigid material that can be easily cleaned and/or sterilized and resists corrosion over time. For example, the base 52 can be poly(methyl methacrylate) (PMMA).

The support 54 is mechanically couplable to the aperture 22 defined by the first and second guides 12a,b, 16a,b such that the first and second guides 12a,b, 16a,b are stationary relative to the base 52. For example, the support 54 can be complementary to the aperture 22 of the tissue stretcher 10 such that the support 54 is movable through the aperture 22 to hold the tissue stretcher 10 fixed in place along the substantially planar surface of the base 52. The support 54 can be dimensioned relative to the aperture 22 such that the support 54 holds the tissue stretcher 10 in place but is removable from the aperture 22 of the tissue stretcher 10 by the application of manual force by an operator.

Referring now to FIGS. 4-6, certain methods of biaxially stretching tissue using the tissue stretcher 10 and the jig 50 are described. The tissue stretcher 10 is mounted to the jig 50 by positioning the support 54 of the jig 50 through the aperture 22 defined by the tissue stretcher 10. This positioning allows the tissue stretcher 10 to be positioned relative to the locking members 56 extending from the base 52. Using gripping portions 30 of the respective first and second mounts 26a,b, 28a,b, an operator can push each of the first and second mounts 26a,b, 28a,b toward one another along the respective first and second guides 12a,b, 16a,b such that the first and second mounts 26a,b, 28a,b are disposed within the area circumscribed by the locking members 56. This has the effect of compressing the respective first and second actuators 32a,b,c,d, 34a,b,c,d such that respective first and second stress loads are set.

The tissue 70 is mounted over hooks 40 extending from the respective first and second mounts 26a,b, 28a,b such that a substantially planar surface of the tissue 70 is parallel to a plane along which the first and second actuators 32a,b,c,d, 34a,b,c,d move. The tissue 70 can be bovine pericardium, equine pericardium, or porcine pericardium. In some embodiments, the tissue 70 is a patch cut from a pericardial sac. In certain embodiments, the tissue 70 has an initial thickness of about 0.1 mm to about 0.7 mm.

With the tissue 70 mounted on the first and second mounts 26a,b, 28a,b, the jig 50 can be moved relative to the tissue stretcher 10 such that the support 54 and the locking members 56 are decoupled from the tissue stretcher 10. For example, the jig 50 can be moved relative to the tissue stretcher 10 such that the support 54 and the locking members are substantially simultaneously decoupled from the tissue stretcher.

The decoupling of the jig 50 from the tissue stretcher 10 allows the first actuators 32a,b,c,d to move the first mounts 26a,b away from one another along the first axis 14 to apply a first set stress load to the tissue 70. Similarly, the decoupling of the jig 50 from the tissue stretcher 10 allows the second actuators 34a,b,c,d to move the second mounds 28a,b away from one another along the second axis 18 to apply a second set stress load to the tissue 70. In some embodiments, the first mounts 26a,b and the second mounts 28 a,b move away from each other substantially simultaneously such that the first and second set stress loads and, thus, first and second stresses are applied to the tissue 70 substantially simultaneously. Additionally or alternatively, the first and second set stress loads applied to the tissue 70 through the relative movement of the first and second mounts 26a,b, 28a,b such that the resulting stresses applied to the tissue 70 can be less than the elastic limit of the tissue 70. In some embodiments, the first and second stress set stress loads is about 0.1 N to about 2 N. In certain embodiments, the first and second set stress applied to the tissue 70 is about 0.01 N/mm$^2$ to about 2 N/mm$^2$.

In some embodiments, the first and second set stress loads are applied to the tissue 70 by the tissue stretcher 10 for about 30 minutes to about 120 minutes (e.g., in a glutaraldehyde solution). In certain embodiments, the tissue can be removed from the tissue stretcher 10 and exposed to a glutaraldehyde solution for about one day to about two weeks. Additionally or alternatively, the tissue 70 can be mounted on the tissue stretcher 10 and exposed to a non-cross linking-solution (e.g., phosphate-buffered saline or saline) for about 30 minutes to about 120 minutes prior to exposure to a glutaraldehyde solution for about one day to about two weeks. The exposure of the tissue 70 to the non-cross linking solution could be carried out between about 4° C. to about 37° C. (e.g., about 20° C.). The exposure of the tissue 70 to the non-cross-linking solution, while the tissue 70 is being biaxially stressed, can allow the tissue 70 to respond to the stress and reorient prior to locking that structure in place with a cross-linking solution such as glutaraldehyde.

As the tissue stretcher 10 acts on the tissue 70 to apply the first and second set stress loads, the tissue stretcher 10 and the tissue 70 can be exposed to a glutaraldehyde solution 80. This exposure can range in duration from about 10 minutes to about 3 hours (e.g., about 30 minutes to about 120 minutes). Such exposure of the tissue 70 to the glutaraldehyde solution 80 can facilitate crosslinking of the tissue 70 such that the tissue 70 will hold the stretched position after the first and second stress loads are removed (e.g., after the tissue 70 is removed from the tissue stretcher 10). In some embodiments, the tissue 70 is held in the stretched position such that the average thickness of the tissue 70 is reduced. For example, the average thickness of the tissue 70 held in the stretched position can be about 0.1 mm to about 0.4 mm. In some implementations, biaxial stretching of tissue and fixing the tissue results in little to no increase in thickness in the tissue. In these embodiments, as compared to fixing tissue under uniaxial stress loading or no stress loading, biaxial stretching can result in thinner fixed tissue. In implementations in which the tissue 70 is part of an intraluminally delivered prosthetic heart valve, such a reduction in the thickness of the tissue 70 can, for example, reduce the sheathing forces associated with the prosthetic heart valve and/or reduce the overall profile of the prosthetic heart valve for easier delivery to the implantation site.

While certain embodiments have been described, other embodiments are possible.

Figure 7:
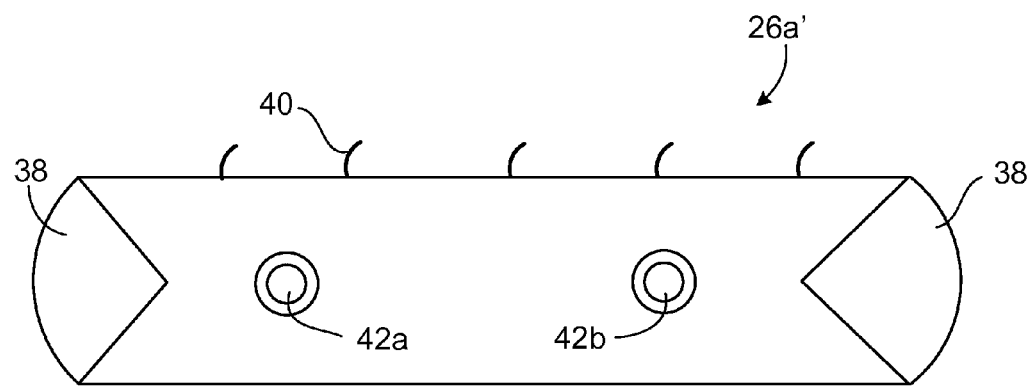
FIG. 7 is a side view of a mount of a tissue stretcher.

For example, while the first and second mounts 26a,b and 28a,b have been described as being movable relative to the respective first and second guides 12a,b, 16a,b through low-friction slidable contact, other embodiments are additionally or alternatively possible. In some embodiments, referring to FIG. 7, a mount 26a' includes bearings 42a,b that can form at least a portion of the moving interface between the mount 26a' and the first guides 12a,b. For example, the bearings 42a,b can be polyoxymethylene or polytetrafluoroethylene such that the bearings 42a,b are grease-free to reduce the likelihood of contamination of the tissue 70. Additionally or alternatively, each bearing 42a,b can be a flange bearing to facilitate placement of the bearings 42a,b on the mount 26a'.

Figure 8:
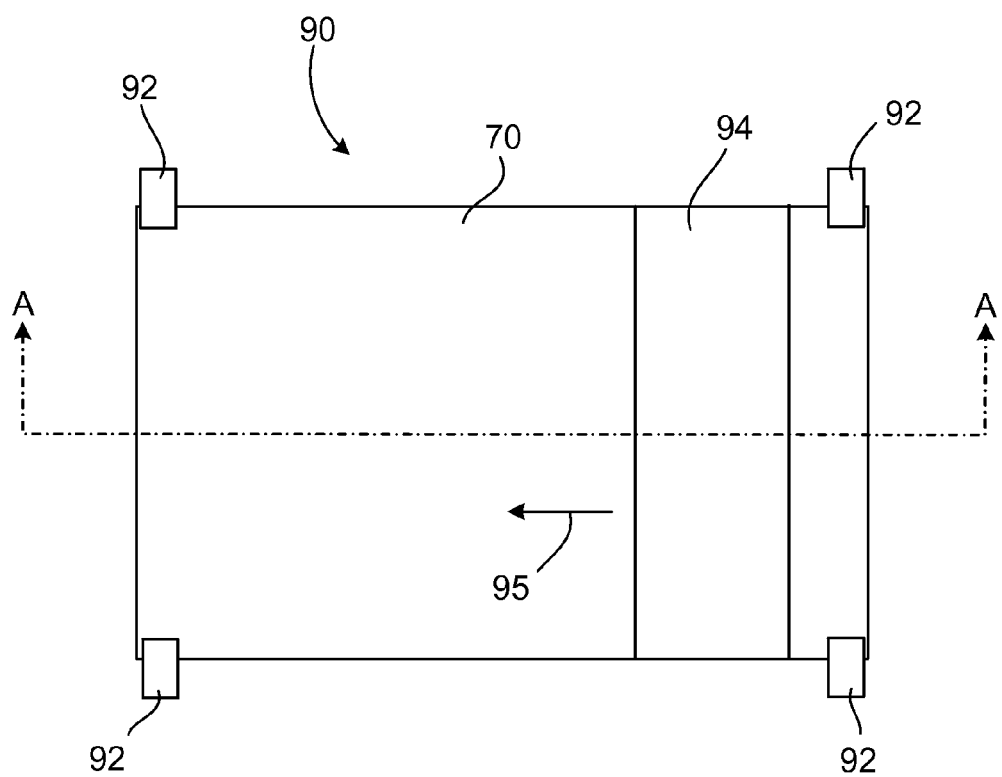
FIG. 8 is a top view of a tissue modification system mounted with tissue.
Figure 9:
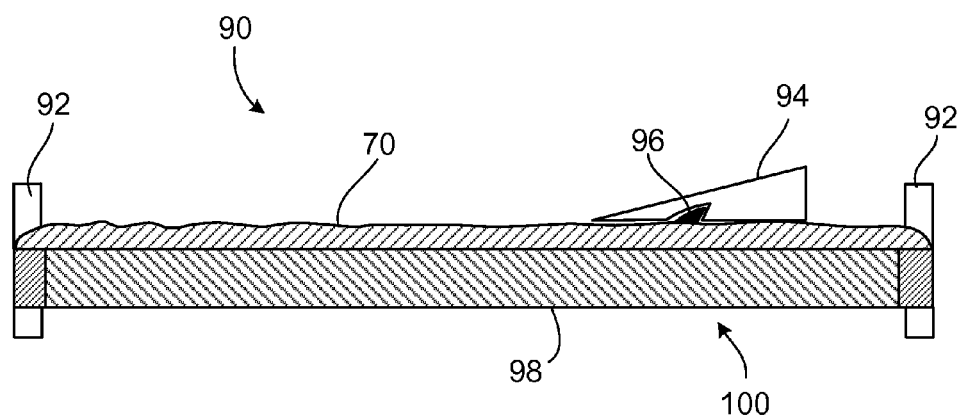
FIG. 9 is a cross-sectional view of the tissue modification system of FIG. 8 taken along the line A-A in FIG. 8.

As another example, while the thickness of the tissue 70 has been described as being reduced through the application of set biaxial stress loads, other embodiments are additionally or alternatively possible. In some embodiments, referring to FIGS. 8-9, a tissue modification system 90 includes a downdraft table 98, clamps 92, and a planar shaver 94. The clamps 92 can secure the tissue 70 (e.g., a substantially planar patch of pericardial tissue) to the downdraft table 98 such that a relatively smooth substantially planar surface of the tissue 70 is disposed toward the table 98 while a relatively rough substantially planar surface of the tissue 70 is disposed toward the planar shaver 94. Vacuum pressure is applied through vents 100 defined by the downdraft table 98. The vacuum pressure draws the tissue 70 toward the substantially planar surface of the table 98 while the planar shaver 94 moves over the tissue 70, for example, in the direction 95 indicated in FIG. 8 such that a blade 96 of the planar shaver 94 removes tissue along at least a portion of the relatively rough substantially planar surface of the tissue 70. Such movement of the planar shaver 94 over the tissue 70 can result in a global reduction of the thickness of the tissue 70. Saline solution can be applied to the tissue 70 to keep the tissue 70 moist throughout the process of mounting the tissue 70 to the table 98 and moving the planar shaver 94 over the tissue 70.

Figure 10:
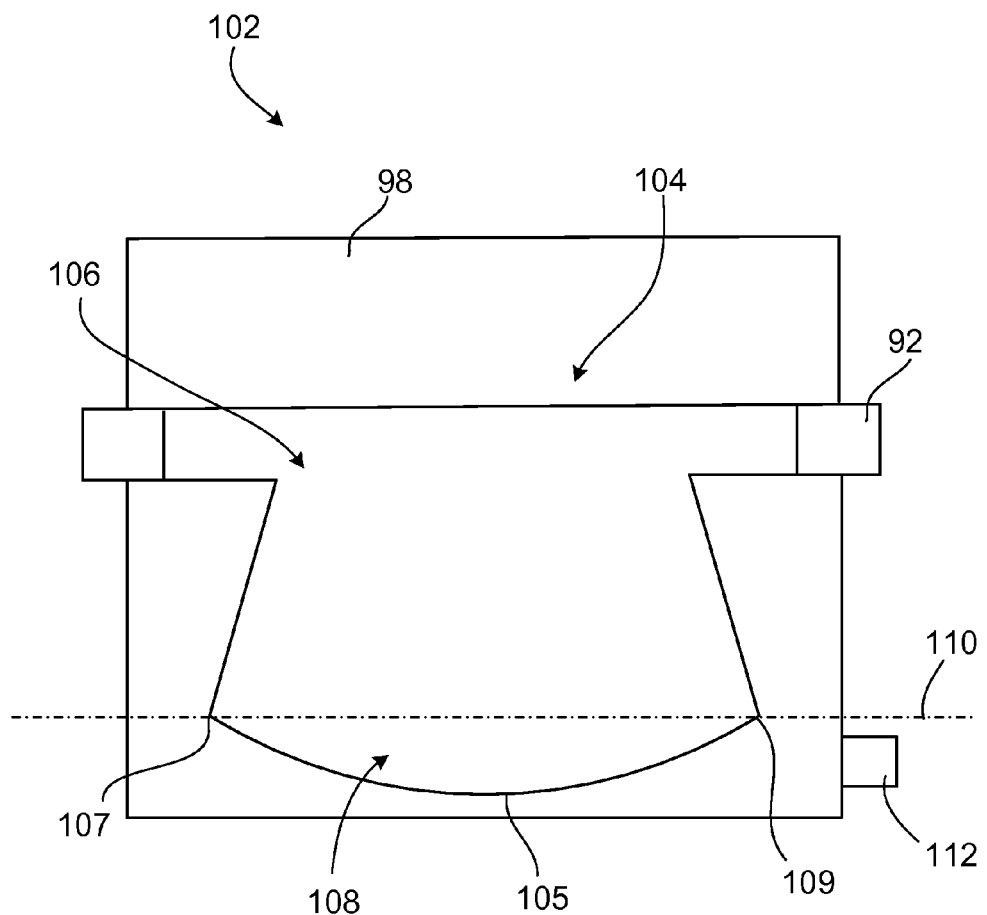
FIG. 10 is a top view of a tissue modification system mounted with a tissue leaflet.

In certain embodiments, referring to FIG. 10, a tissue modification system 102 includes a laser 112 (e.g., a femtosecond laser) proximate to the table 98 to direct a laser beam across at least a portion of a leaflet 104 clamped by clamps 92 to the table 98. For example, the leaflet 104 can be a leaflet of a prosthetic heart valve, and the leaflet can include a coaptation portion 106 substantially opposite an arcuate edge 105 having a first end 107 and a second end 109. The leaflet 104 can also include a belly 108 extending from the arcuate edge 105 to an axis 110 defined by the first and second ends 107, 109 of the arcuate edge 105.

The laser 112 can, for example, direct the laser beam across the leaflet 104 to remove tissue locally along a portion of the leaflet 104 to achieve a thickness profile in which portions of the leaflet 104 may be thinner than portions of the leaflet 104. For example, the laser 112 can direct the laser beam across the leaflet 104 to remove tissue from the belly 108 of the leaflet 104. Such local removal of tissue from the leaflet 104 can, for example, reduce the forces associated with sheathing a prosthetic heart valve including the leaflet 104 as compared to a leaflet without material removed from its respective belly.

As still another example, while tissue stretching and tissue removal have been described for reducing the forces associated with sheathing a prosthetic heart valve including one or more tissue leaflets, other embodiments are additionally or alternatively possible. For example, FIGS. 11A-11D illustrate a prosthetic heart valve 112 that includes tissue 114 (e.g., one or more leaflets movable between open and closed positions to permit and restrict, respectively, the flow of blood through the heart) and a sheath 120 that can be used for intraluminal delivery of the prosthetic heart valve 112. The prosthetic heart valve 112 can be stored initially in a first solution 116 that is isotonic with the tissue 114. For example, the prosthetic heart valve 112 can be shipped in the first solution 116. The prosthetic heart valve 112 can be exposed to a second solution 118 (e.g, in the operating room just prior to implantation of the prosthetic heart valve 112) such that water in the tissue 114 flows out of the tissue 114 to reduce at least one dimension of the tissue 114.

For example, the second solution 118 can be a solution hypertonic to the tissue 114. In some embodiments, the second solution 118 is about 75 percent to about 80 percent water. Additionally or alternatively, the tonicity (e.g., hypertonicity) of the second solution 118 is about 339 mOsm/L (110% of isotonic, ~10 g/L) to about the limit of solubility of NaCl in water, 12.3 Osm/L (40× isotonic, 359 g/L).

Additionally or alternatively, the second solution 118 can include alcohol. For example, the exposure of the tissue 114 to the second solution 118 can include exposure of the tissue 114 to a series of graded alcohol solutions (e.g., about 50%, about 60%, about 70%, about 90%, about 95%, about 100%) to remove water and thin the tissue 114 prior to loading the tissue. Additionally or alternatively, exposure of the tissue 114 to the second solution 118 can include exposures of the tissue 114 to a series of graded ethylene glycol solutions (e.g., about 50%, about 60%, about 70%, about 90%, about 95%, about 100%) to remove water and thin the tissue 114 prior to loading. In some embodiments, the tissue 114 is exposed to alcohol or ethylene glycol solutions prior to stress loading the tissue 114.

In some embodiments, the tissue 114 can be exposed to the second solution 118 as an acute rinse (e.g., for about 30 seconds to about 15 minutes). In certain embodiments, the tissue 114 can be stored in the second solution 118 to eliminate, for example, the need for a rinse. The first solution 116 and the second solution 118 can be at substantially the same temperature (e.g., room temperature) which, as compared to techniques that require exposing tissue of a prosthetic heart valve to solutions at different temperatures, can reduce the need for the end-user to maintain a controlled difference in temperature to achieve a desired reduction in the size of tissue of a prosthetic heart valve.

In some embodiments, removal of water from the tissue 114 through exposure to the second solution 118 is done immediately prior to sheathing the valve 112. In certain embodiments, removal of water from the tissue 114 through exposure to the second solution 118 is done some time prior to sheathing the valve 112. For example, the tissue 114 can be exposed to the second solution 118 during the final manufacturing of the valve 112 that includes the tissue 114. Through exposure of the tissue 114 to the second solution 118 during the final manufacturing of the valve 112, the tissue 114 can, for example, undergo terminal sterilization in a dehydrated state. As compared to tissue 114 in a hydrated state, the tissue 114 in a dehydrated state can better withstand exposure to forms of terminal sterilization that tend to damage and/or alter tissue 114 in a hydrated state. For example, terminal sterilization of the tissue 114 in the dehydrated state can include exposure of the dehydrated tissue to electron beam (e-beam) and/or ethylene oxide (EtO). Additionally or alternatively, with the tissue 114 in the dehydrated state, the valve 112 could be sheathed or unsheathed during sterilization and storage, and the entire assembly (including the valve 112, a delivery system, and a handle) could be sterilized in one package, without the need for storing the valve in liquid.

With the size of the tissue 114 reduced through exposure to the second solution 118, the sheath 120 can be advanced distally to sheath the prosthetic heart valve 112 for intraluminal delivery to an implantation site in a patient. As compared to tissue that has not been exposed to the second solution 118, the force required to sheath the tissue 114 will be reduced. Upon implantation and exposure to blood in the patient, the tissue 114 will absorb water to return to its original size.

A number of embodiments of the invention have been described. Nevertheless, it will be understood that various modifications may be made without departing from the spirit and scope of the invention. For example, the first and second guides can each be a single rod or three or more rods. Accordingly, other embodiments are within the scope of the following claims.

What is claimed is:

1. A tissue modification system comprising:
a tissue stretcher comprising
a first guide defining a first axis and
a second guide defining a second axis intersecting the first axis;
a first set of mounts and a second set of mounts, the first set of mounts movable relative to one another along the first axis, the second set of mounts movable relative to one another along the second axis,
the tissue stretcher defining an aperture; and
a jig comprising a base and a support extending from the base, wherein at least a portion of the support is engageable with the aperture to hold at least one of the first and second guides stationary relative to the base.

2. The tissue modification system of claim 1, the aperture located where the first axis and the second axis intersect.

3. The tissue modification system of claim 1, the first guide and second guide mechanically coupled where the first axis and the second axis intersect.

4. The tissue modification system of claim 1, each of the first and second guides comprising one or more rods.

5. The tissue modification system of claim 1, wherein the aperture is substantially rectangular.

6. The tissue modification system of claim 1, the first and second set of mounts configured to transmit a stress load to a piece of tissue.

7. The tissue modification system of claim 1, further comprising a first actuator and a second actuator to generate stress loads.

8. The tissue modification system of claim 1, wherein the first and second actuators comprise springs.

9. A tissue modification system comprising:
a tissue stretcher comprising
a first guide defining a first axis and
a second guide defining a second axis intersecting the first axis;
a first set of mounts and a second set of mounts, wherein at least one mount in the first set of mounts is movable relative to the other mount along the first axis, wherein at least one mount in the second set of mounts is movable relative to the other mount along the second axis,
the tissue stretcher configured to deliver a first stress load to a piece of tissue along the first axis and a second stress load to the piece of tissue along the second axis.

10. The tissue modification system of claim 9, wherein the first stress load is transmitted to the piece of tissue through the first set of mounts and the second stress load is transmitted to the piece of tissue through the second set of mounts.

11. The tissue modification system of claim 9, each of the first and second guides comprising one or more rods.

12. The tissue modification system of claim 9, the tissue stretcher further defining an aperture.

13. The tissue modification system of claim 9, the aperture located where the first axis and the second axis intersect.

14. The tissue modification system of claim 9, further comprising a first actuator and a second actuator to generate stress loads.

15. The tissue modification system of claim 9, wherein the first and second actuators comprise springs.

16. A tissue modification method comprising:
coupling a piece of tissue to at least a first mount and at least a second mount of a tissue modification apparatus, the first mount being movable along a first guide defining a first axis and the second mount being movable along a second guide defining a second axis, the first axis being nonparallel to the second axis;
applying a first stress load to the piece of tissue along the first axis;
applying a second stress load to the piece of tissue along the second axis substantially perpendicular to the first axis, wherein the first and second stress loads are applied to the tissue substantially simultaneously; and
exposing the tissue to a crosslinking solution while the first and second stress loads are applied.

17. The tissue modification method of claim 16, the crosslinking solution comprising a glutaraldehyde solution.

18. The tissue modification method of claim 16, wherein the tissue is exposed to a crosslinking solution for a period of about one day to two weeks.

19. The tissue modification method of claim 16, wherein the average thickness of the tissue when the first and second stress loads are applied is between 0.1 mm and 0.4 mm.

20. The tissue modification method of claim 16, wherein the tissue is also exposed to a non-crosslinking solution.

\* \* \* \* \*